US00PP19009P2

(12) United States Plant Patent
Cesarini

(10) Patent No.: US PP19,009 P2
(45) Date of Patent: Jul. 8, 2008

(54) *THUJA* PLANT NAMED 'CONGABE'

(50) Latin Name: *Thuja occidentalis*
Varietal Denomination: Congabe

(75) Inventor: Gabriel Cesarini, Denton, MD (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/798,025

(22) Filed: May 9, 2007

(51) Int. Cl.
*A01H 5/00* (2006.01)

(52) U.S. Cl. ..... Plt./213

(58) Field of Classification Search ..... Plt./213, Plt./226
See application file for complete search history.

*Primary Examiner*—Kent L. Bell
*Assistant Examiner*—Annette H Para
(74) *Attorney, Agent, or Firm*—Buchanan Ingersoll & Rooney PC

(57) ABSTRACT

A new *Thurja occidentalis* (i.e., American Arborvitae) plant is provided which originated as a branch mutation of the 'Rheingold' variety (non-patented in the United States). Unlike the parental variety, the new plant displays distinctive foliage coloration which is reddish at the tips when grown under full sun conditions. A rounded growth habit and good winter hardiness are displayed. The plant is well suited for providing attractive and colorful ornamentation.

2 Drawing Sheets

Botanical/commercial classification: *Thuja occidentalis/ THUJA* Plant.
Varietal denomination: cv. Congabe

SUMMARY OF THE INVENTION

Many varieties of *Thuja occidentalis* plants (i.e., American Arborvitae plants) are known in the horticultural industry. Among these is the "Rheingold" variety (non-patented in the United States) which is known to display bright yellow-green foliage when both juvenile and mature that commonly turns to a bronze coloration during the water.

The new variety was discovered as a distinctive branch mutation of unknown causation on a single plant of the 'Rheingold' variety growing at the home of the originator at Denton, Md. U.S.A. The new variety was observed to display a highly distinctive foliage coloration during the growing season. Had the new variety not been discovered and preserved it would have been lost to mankind.

It was found that the new *Thuja* plant of the present invention possesses the following combination of characteristics:

(a) displays foliage having reddish coloration at the tips during the growing season under full sun conditions unlike the yellow-green foliage coloration of the 'Rheingold' variety (non-patented in the United States), (b) exhibits rounded growth habit, (c) resists sun and winter burning, (d) displays good winter hardiness, and (e) is well suited for growing as attractive ornamentation.

When grown in shaded locations the foliage of the new variety is more green in coloration.

The new variety of the present invention can be readily distinguished from its 'Rheingold' variety parent and all other *Thuja* varieties known to the discoverer in view of its distinctive foliage coloration. More specifically, the foliage of the new variety is much redder in coloration when grown in full sun throughout the entire year.

The new variety is well suited for providing attractive colorful ornamentation in gardens and in the landscape over an extended period of time.

Asexual reproduction of the new variety at West Grove, Pa., U.S.A., beginning in 2003, by the use of softwood cuttings has demonstrated that the distinctive characteristics of the new variety of the present invention are reliably transmitted from one generation to another. Accordingly, the new variety reproduces in a true-to-type manner by such technique.

The new variety has been named 'Congabe' and will be marketed under the FIRE CHIEF trademark.

BRIEF DESCRIPTION OF THE PHOTOGRAPHS

The accompanying photographs show as true as it is reasonably possible to make the same in color illustrations of this character typical specimens of the new variety of the present invention. The depicted plants were growing in containers outdoors under full sun at West Grove, Pa., U.S.A.

DETAILED DESCRIPTION

Figure 1:
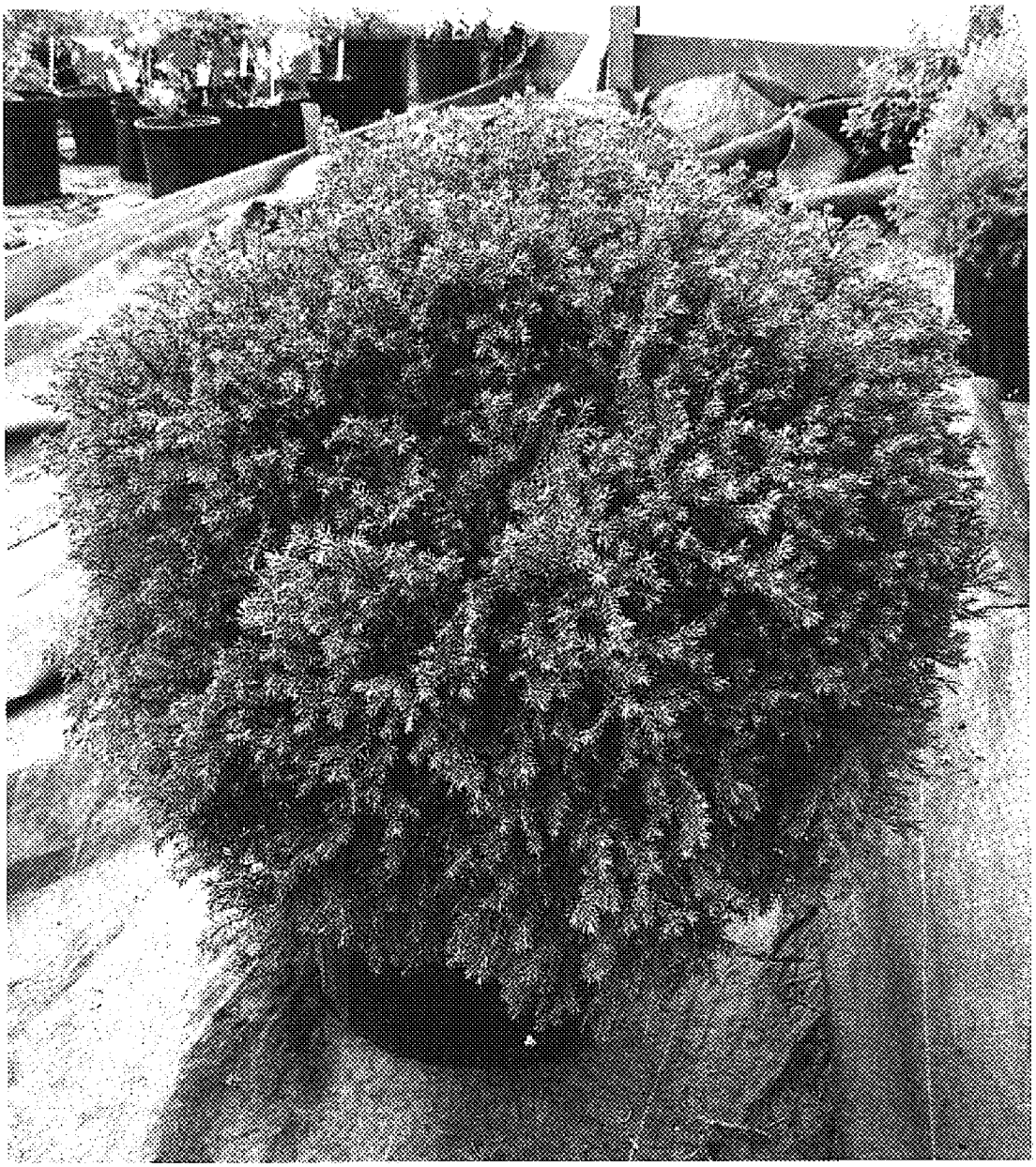
FIG. 1 illustrates a close view of a typical specimen of the new variety. The rounded growth habit and distinctive reddish foliage coloration are shown.
Figure 2:
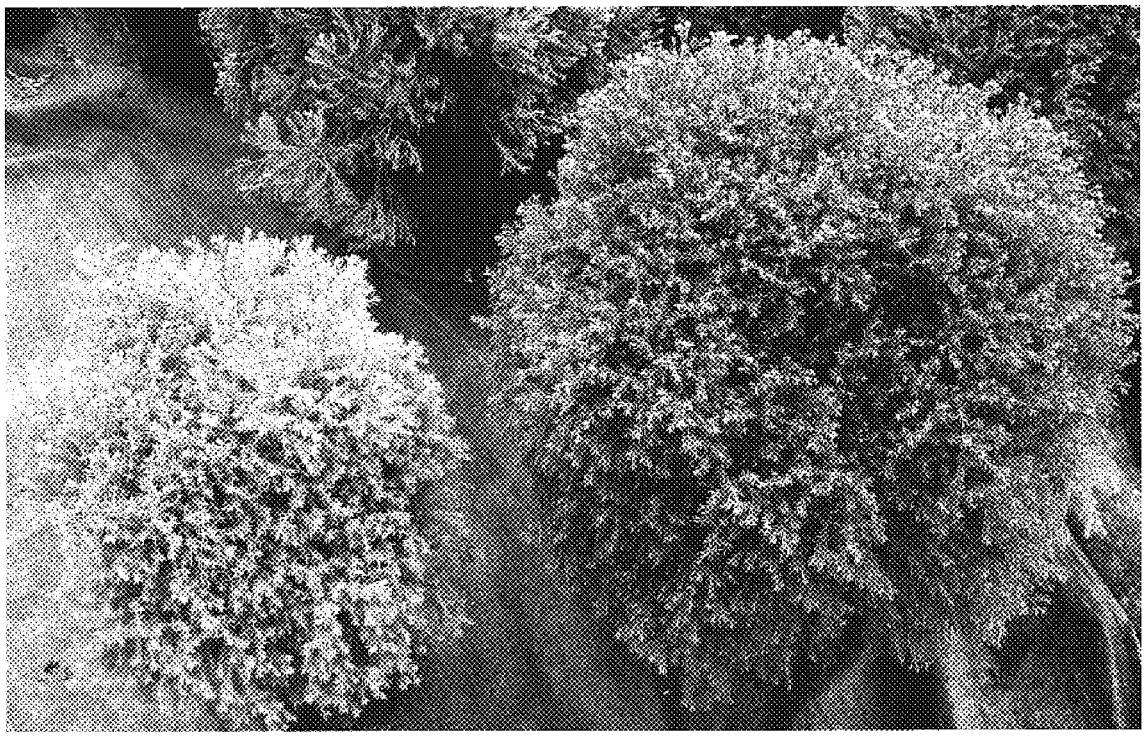
FIG. 2 illustrates for comparative purposes typical specimens of the 'Congabe' variety (right) and the parental 'Rheingold' variety (left).

The following description is based upon the observation of typical plants of the new variety at an age of approximately three years during the summer of 2006 while growing in containers in full sun at West Grove, Pa., U.S.A. The growing conditions approximated those employed for the commercial production of *Thuja* plants. The chart used in the identification of colors is the R.H.S. Colour Chart of The Royal Horticultural Society, London, England. Common color terms are to be accorded their customary dictionary significance.

Plant:

*Height.*—Approximately 130 to 150 cm at maturity.

*Width.*—Approximately 90 to 110 cm at maturity.

*Growth habit.*—Rounded, perennial evergreen shrub.

*Branching.*—Multiple generally upright main stems commonly arise from the base (e.g., approximately 4 to 6 in number), secondary branches emerge from main stems (e.g., approximately 2 to 4 in number), and many small sprays emerge from secondary stems and curve upwards.

*Branching/habit.*—Freely branching with the branches being horizontal to arching, branchlets are borne in the same plane and commonly are loosely pendulous towards the apices, and the branches and foliage are maintained to the soil level.

*Main stems.*—Approximately 120 cm in length and approximately 1 cm in diameter woody and flaky, and Greyed. Orange Group 177B in coloration.

*Branches.*—Approximately 42 cm in length and approximately 5 mm in diameter, smooth, and Greyed-Orange Group 177B in coloration.

*Spray size.*—Commonly approximately 20 cm in length, and approximately 15 cm in width.

*Branchlets.*—Commonly approximately 11 to 15 cm in length, approximately 4 to 6 cm in width, approximately 2 mm in diameter, fuzzy texture, and Yellow-Green Group 152B in coloration.

*Internode length.*—On main and secondary stems approximately 0.5 to 2 cm, between sprays approximately 0.5 to 2 cm, and between branchlets approximately 0.25 to 1 cm.

*Roots.*—Dense and freely branching.

Foliage:

*Arrangement.*—Alternate or opposite, commonly borne in two ranks of opposite pairs (i.e., 4-ranked).

*Form.*—Simple, needle-like, and densely imbricate.

*Leaf size.*—Commonly approximately 7 mm in length and approximately 2 mm in width.

*Leaf quantity.*—Commonly approximately 200 to 300 leaves per branchlet, and approximately 8 to 12 branchlets per spray.

*Apex.*—Acute.

*Base.*—Cordate.

*Venation.*—Not apparent.

*Margin.*—Entire.

*Texture.*—On upper and lower surfaces glabrous and slightly glaucous.

*Color.*—When in full sun, Greyed-Red Group 178D on the upper and under surfaces, and when in the shade, Yellow-Green Group 144A on the upper and under surfaces.

*Fragrance.*—Somewhat acrid when crushed.

Development:

*Resistance to disease.*—Not observed to be resistant to disease common to *Thuja* plants.

*Resistance to pests.*—Not observed to be resistant to pests common to *Thuja* plants.

*Weather tolerance.*—Has been observed to be tolerant to drought, rain and wind at temperatures ranging from −25° to 30° C.

The new 'Congabe' variety has not been observed to date under all possible environmental conditions. Accordingly, it is possible that the phenotype may vary somewhat with variations in the environment, such as temperature, light intensity, day length, and other cultural conditions without variance of the genotype.

I claim:

1. A new and distinct *Thuja* plant having the following combination of characteristics:

(a) displays foliage having reddish coloration at the tips during the growing season under full sun conditions unlike the yellow-green foliage coloration of the 'Rheingold' variety (non-patented in the United States), (b) exhibits a rounded growth habit, (c) resists sun and winter burning, (d) displays good winter hardiness, and (e) is well suited for growing as attractive ornamentation; substantially as illustrated and described.

* * * * *